(12) United States Patent
Kawaguchi et al.

(10) Patent No.: US 8,399,722 B2
(45) Date of Patent: Mar. 19, 2013

(54) PROCESS FOR PRODUCING 2,3,3,3-TETRAFLUOROPROPENE

(75) Inventors: Satoshi Kawaguchi, Tokyo (JP); Hidekazu Okamoto, Tokyo (JP); Yu Takeuchi, Tokyo (JP); Hirokazu Takagi, Tokyo (JP); Kunio Watanabe, Tokyo (JP); Koichi Yanase, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 13/167,235

(22) Filed: Jun. 23, 2011

(65) Prior Publication Data

US 2011/0319681 A1  Dec. 29, 2011

Related U.S. Application Data

(60) Provisional application No. 61/365,966, filed on Jul. 20, 2010.

(30) Foreign Application Priority Data

Jun. 23, 2010  (JP) ................ 2010-142665

(51) Int. Cl.
*C07C 19/08* (2006.01)
(52) U.S. Cl. .................................. 570/176
(58) Field of Classification Search .......... None
See application file for complete search history.

(56) References Cited

U.S. PATENT DOCUMENTS

| 2010/0022808 A1 | 1/2010 | Rao et al. |
| 2010/0204529 A1 | 8/2010 | Terada et al. |

FOREIGN PATENT DOCUMENTS

| EP | 396974 A1 * | 11/1990 |
| JP | 02-286635 | 11/1990 |
| JP | 2010-510221 | 4/2010 |
| JP | 2010-513517 | 4/2010 |
| WO | WO 2008/060614 | 5/2008 |
| WO | WO 2009/035130 A2 | 3/2009 |

OTHER PUBLICATIONS

U.S. Appl. No. 13/167,464, filed Jun. 23, 2011, Takagi, et al.
U.S. Appl. No. 13/167,455, filed Jun. 23, 2011, Okamoto.
U.S. Appl. No. 13/167,285, filed Jun. 23, 2011, Seki, et al.
U.S. Appl. No. 13/167,509, filed Jun. 23, 2011, Kawaguchi, et al.
U.S. Appl. No. 13/167,145, filed Jun. 23, 2011, Takagi, et al.
U.S. Appl. No. 13/167,254, filed Jun. 23, 2011, Kawaguchi, et al.
International Search Report issued Jul. 26, 2011, in PCT/JP2011/064423 (with Translation of Category of Cited Documents).

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

The object is to provide a process for producing highly pure 2,3,3,3-tetrafluoropropene, whereby formation of 3,3,3-trifluoropropene as a by-product is suppressed.
A process for producing 2,3,3,3-tetrafluoropropene, which comprises introducing and reacting a raw material compound composed of at least one of 1,1-dichloro-2,3,3,3-tetrafluoropropene and 1-chloro-2,3,3,3-tetrafluoropropene, and hydrogen, in a catalyst layer packed with a catalyst-supporting carrier, wherein the temperature of the catalyst layer is controlled to be higher than the dew point of the raw material mixed gas comprising the raw material compound and the hydrogen, and the maximum temperature of the catalyst layer is maintained to be at most 130° C. during the reaction.

12 Claims, 2 Drawing Sheets

PROCESS FOR PRODUCING 2,3,3,3-TETRAFLUOROPROPENE

TECHNICAL FIELD

The present invention relates to a process for producing 2,3,3,3-tetrafluoropropene.

BACKGROUND ART 2,3,3,3-tetrafluoropropene ($CF_3CF=CH_2$, HFO-1234yf) contains no chlorine and thus is useful as an alternative compound for chlorofluorocarbons to be used for e.g. refrigerants.

As a process for producing HFO-1234yf, a process may, for example, be mentioned wherein 1,1-dichloro-2,2,3,3,3-pentafluoropropane ($CF_3CF_2CHCl_2$, HCFC-225ca) is subjected to a dehydrofluorination reaction to obtain 1,1-dichloro-2,3,3,3-tetrafluoropropene ($CF_3CF=CCl_2$, CFO-1214ya), and then, CFO-1214ya is reacted with hydrogen and reduced to obtain HFO-1234yf.

As a method of reducing CFO-1214ya to obtain HFO-1234yf, the following method (i) may, for example, be mentioned.

(i) A method for obtaining HFO-1234yf by reacting CFO-1214ya with hydrogen at a temperature of from 100 to 400° C. in the presence of a catalyst having palladium supported on alumina (Patent Document 1).

However, the method (i) has a problem such that together with HFO-1234yf, an excessively reduced product 3,3,3-trifluoropropene ($CF_3CH=CH_2$, HFO-1243zf) will be formed as a by-product which has a boiling point close to HFO-1234yf and thus cannot be separated therefrom by distillation.

On the other hand, as a method for carrying out a similar reduction reaction, the following method (ii) has been proposed.

(ii) a method of reacting $RfCF=CX_2$ (wherein Rf is a $C_{1-10}$ fluoroalkyl group, and X is chlorine, bromine or iodine) with hydrogen at a temperature of from 5 to 200° C. in the presence of a catalyst having palladium supported on active carbon, to obtain $RfCF=CH_2$ (Patent Document 2).

However, also by the method (ii), together with the desired product $RfCF=CH_2$, an excessively reduced product $RfCH=CH_2$ may sometimes be formed as a by-product. For example, in a case where Rf is $H(CF_2)_3-$, there is a certain difference in boiling point between the desired product and the by-product, and they can be separated by distillation. However, in a case where Rf is $CF_3-$, i.e. in a case where the desired product is HFO-1234yf, as mentioned above, the desired product and the by-product cannot be separated by distillation.

Prior Art Documents

Patent Documents

Patent Document 1: WO2008/060614
Patent Document 2: JP-A-2-286635

DISCLOSURE OF INVENTION

Technical Problem

It is an object of the present invention to provide a process for producing highly pure 2,3,3,3-tetrafluoropropene (HFO-1234yf), whereby formation of HFO-1243zf as a by-product is suppressed.

Solution to Problem

In order to solve the above problem, the present invention has adopted the following construction.

[1] A process for producing 2,3,3,3-tetrafluoropropene, which comprises introducing and reacting a raw material compound composed of at least one of 1,1-dichloro-2,3,3,3-tetrafluoropropene and 1-chloro-2,3,3,3-tetrafluoropropene, and hydrogen, in a gas phase in a catalyst layer packed with a catalyst-supporting carrier, wherein the temperature of the catalyst layer is controlled to be higher than the dew point of the raw material mixed gas comprising the raw material compound and the hydrogen, and the maximum temperature of the catalyst layer is maintained to be at most 130° C. during the reaction.

[2] The process for producing 2,3,3,3-tetrafluoropropene according to the above [1], wherein the temperature of the catalyst layer is at least 50° C.

[3] The process for producing 2,3,3,3-tetrafluoropropene according to the above [1] or [2], wherein the catalyst is palladium, and the carrier is active carbon.

[4] The process for producing 2,3,3,3-tetrafluoropropene according to the above [3], wherein the amount of the palladium supported is from 0.1 to 10 mass % based on the active carbon.

[5] The process for producing 2,3,3,3-tetrafluoropropene according to any one of the above [1] to [4], wherein the packed density of the catalyst-supporting carrier in the catalyst layer is from 0.5 to 1 $g/cm^3$.

[6] The process for producing 2,3,3,3-tetrafluoropropene according to any one of the above [1] to [5], wherein the catalyst layer is maintained to be at most 80° C. except for the reaction zone of the raw material mixed gas and its vicinity in the catalyst layer during the reaction.

[7] The process for producing 2,3,3,3-tetrafluoropropene according to any one of the above [1] to [6], wherein the raw material mixed gas further contains an inert gas.

[8] The process for producing 2,3,3,3-tetrafluoropropene according to any one of the above [1] to [7], wherein in the raw material mixed gas, the ratio of the number of moles of hydrogen to the number of moles of chlorine atoms in the raw material compound ($H_2$/Cl) is adjusted to be at most 0.7.

[9] The process for producing 2,3,3,3-tetrafluoropropene according to any one of the above [1] to [7], wherein the hydrogen is introduced, as divided, to at least two positions in the catalyst layer.

[10] The process for producing 2,3,3,3-tetrafluoropropene according to the above [9], wherein the ratio of the total amount of hydrogen to the total amount of the raw material compound introduced to the catalyst layer is adjusted to be at most 0.7 by the ratio of the number of moles of hydrogen to the number of moles of chlorine atoms in the raw material compound ($H_2$/Cl).

[11] The process for producing 2,3,3,3-tetrafluoropropene according to any one of the above [1] to [10], wherein the linear velocity u of the raw material mixed gas represented by the following formula (I) in the catalyst layer is from 1 to 30 cm/sec.:

$$u = (W/100) \times V/S \quad (I)$$

(In the formula (I), W is the concentration (mol %) of the raw material compound in the entire gas flowing in the catalyst layer, V is the flow rate ($cm^3$/sec.) of the entire gas flowing in the catalyst layer, and S is the cross-sectional area (cm²) of the catalyst layer to the flow direction of the gas.)

Advantageous Effects of Invention

According to the process of the present invention, it is possible to suppress formation of HFO-1243zf as a by-product and to obtain highly pure HFO-1234yf.

DESCRIPTION OF EMBODIMENT

Figure 1:
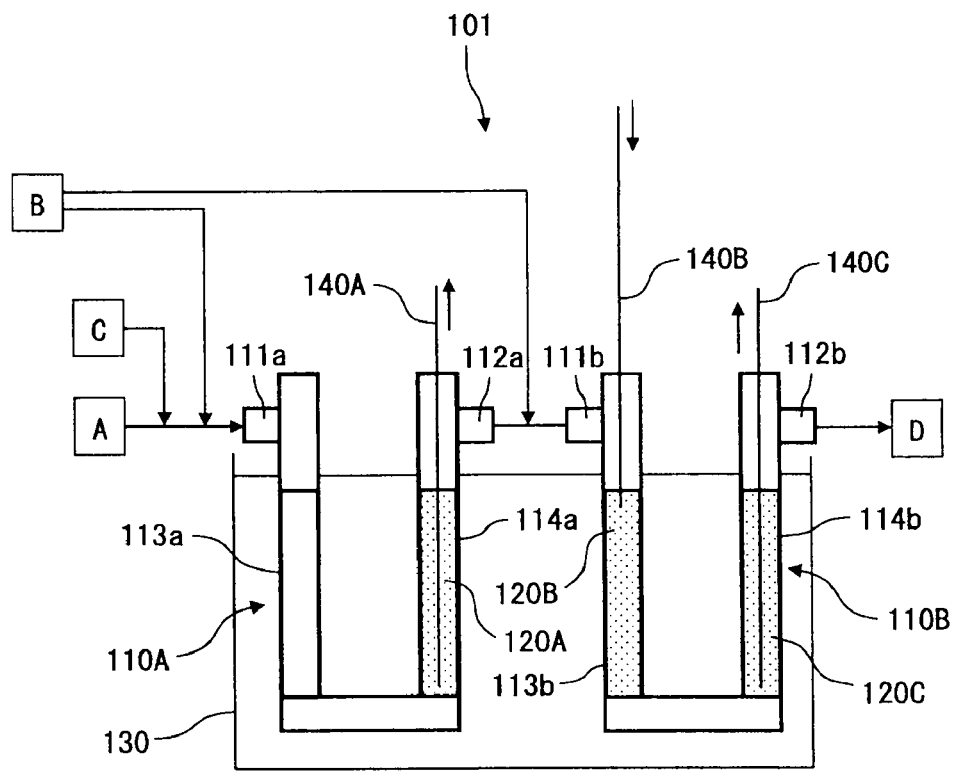
FIG. 1 is a schematic view illustrating a reaction apparatus used in Examples.

In the process for producing 2,3,3,3-tetrafluoropropene ($CF_3CF=CH_2$, HFO-1234yf) of the present invention, a raw material compound composed of at least one of 1,1-dichloro-2,3,3,3-tetrafluoropropene ($CF_3CF=CCl_2$, CFO-1214ya) and 1-chloro-2,3,3,3-tetrafluoropropene ($CF_3CF=CHCl$, HCFO-1224yd), and hydrogen, are introduced and reacted in a catalyst layer packed with a catalyst. That is, the process of the present invention is a process to obtain HFO-1234yf by subjecting the raw material compound and hydrogen to a gas phase reaction in the presence of a catalyst. The process of the present invention is characterized in that the temperature of the catalyst layer is controlled to be higher than the dew point of the raw material mixed gas comprising the raw material compound and the hydrogen, and the maximum temperature of the catalyst layer is maintained to be at most 130° C.

CFO-1214ya and HCFO-1224yd will form HFO-1234yf by the reactions represented by the following formulae (1) and (2), respectively.

$$CF_3CF=CCl_2+2H_2 \rightarrow CF_3CF=CH_2+2HCl \quad (1)$$

$$CF_3CF=CHCl+H_2 \rightarrow CF_3CF=CH_2HCl \quad (2)$$

As the catalyst, a palladium catalyst is preferred, and the palladium catalyst is preferably employed as supported on a carrier. The palladium catalyst may be not only a palladium simple substance but also a palladium alloy. Further, it may be a mixture of palladium with another metal or a composite catalyst having palladium and another metal separately supported on carriers. The palladium alloy catalyst may, for example, be a palladium/platinum alloy catalyst or a palladium/rhodium alloy catalyst.

As the carrier, active carbon or a metal oxide such as alumina, zirconia or silica, may, for example, be mentioned. Among them, active carbon is preferred from the viewpoint of the durability and reaction selectivity. That is, the catalyst in the present invention is preferably a palladium catalyst supported on active carbon.

The active carbon may be one prepared by using, as a raw material, wood, charcoal, fruit shell, coconut shell, peat, lignite, coal or the like, and one obtained from a plant raw material rather than from a mineral raw material is preferred. Particularly preferred is coconut shell active carbon.

As the shape of the carrier, briquette having a length of from about 2 to 5 mm, pulverized coal of from about 4 to 50 mesh or granular coal may, for example, be mentioned. Among them, pulverized coal of from 4 to 20 mesh or briquette is preferred.

The supported amount of palladium based on active carbon is preferably from 0.1 to 10 mass %, more preferably from 0.5 to 1 mass %. When the supported amount of palladium is at least the lower limit value, the conversion of the raw material and hydrogen will be improved. When the above supported amount of palladium is at most the upper limit value, an excessive temperature rise of the catalyst layer by a heat of reaction can easily be controlled, and formation of by-products can easily be reduced.

Further, the palladium supporting carrier may further have a metal other than palladium supported.

The metal other than palladium may, for example, be a Group 8 element such as iron, ruthenium or osmium; a Group 9 element such as cobalt, rhodium or iridium; a Group 10 element such as nickel or platinum; or gold. Such metals other than palladium may be used alone, or two or more of them may be used in combination.

The proportion of the metal other than palladium is preferably from 0.01 to 50 parts by mass, per 100 parts by mass of palladium. The composite catalyst having the metal other than palladium supported together with palladium tends to have higher catalyst durability than the catalyst having only palladium supported alone.

In the present invention, the catalyst layer is formed by packing the above catalyst-supporting carrier in a reactor. The packed density of the catalyst-supporting carrier in the catalyst layer is preferably from 0.5 to 1 g/cm³, more preferably from 0.6 to 0.8 g/cm³. When the packed density of the catalyst-supporting carrier is at least the lower limit value, the packed amount of the catalyst-supporting carrier per unit volume is large, whereby the amount of gas to be reacted can be increased, and the productivity will be improved. When the packed density of the catalyst-supporting carrier is at most the upper limit value, the temperature rise of the catalyst layer can easily be controlled, and it becomes easy to maintain the reaction temperature to be at most 130° C.

In the reactor, there may be one or more portions packed with the catalyst-supporting carrier.

In the catalyst layer, a region (reaction zone) where the raw material mixed gas is reacted tends to have a temperature higher than other regions, due to generation of heat of reaction. In the present invention, "The maximum temperature of the catalyst layer during the reaction" is meant for the temperature of the region showing the highest temperature among temperatures in the reaction zone and its periphery in the catalyst layer. Other than this reaction zone and its periphery is considered to be a region where the raw material mixed gas or the formed gas is flowing without being substantially involved in the reaction, and the temperature of such a region is simply referred to as the temperature of the catalyst layer. In the present invention, it is preferred to bring the catalyst layer to a predetermined temperature immediately before initiating the introduction of the raw material mixed gas to the catalyst layer, and the temperature at that time is the temperature of the catalyst layer at the initiation of the reaction. Further, after the initiation of the reaction by introducing the raw material mixed gas, the temperature of the catalyst layer may be changed. For example, in a case where the activity of the catalyst has started to decrease, the temperature of the catalyst layer may be increased.

In order to adjust the temperature of the catalyst layer, it is common to heat the reactor packed with the catalyst-supporting carrier, from outside. The temperature of the catalyst layer may be adjusted by adjusting the temperature of the heating medium to heat the reactor.

The temperature of the catalyst layer is adjusted to be higher than the dew point of the raw material mixed gas, since the reaction is a gas phase reaction. Further, if the raw material compound is reacted in a liquefied state with hydrogen, formation of byproducts (such as HFO-1243zf) by excessive reduction of HFO-1234yf is likely to increase. Specifically, it is preferred that in such a state that the catalyst layer is heated to at least 50° C., the raw material mixed gas is introduced and reacted in the catalyst layer, since the boiling point of CFO-1214ya is 46° C. and the boiling point of HCFO-1224yd is assumed to be from 4 to 10, and from the viewpoint of the reactivity. The temperature of the catalyst layer is more preferably at least 60° C. from the viewpoint of the improvement of the conversion.

Further, the temperature of the catalyst layer gradually decreases along with the progress of deterioration of the catalyst, whereby the conversion may decrease. Therefore, it is preferred to carry out an operation to gradually increase the catalyst temperature and to maintain the temperature of the catalyst layer at a sufficient temperature level, so that a high conversion can be maintained.

Further, in the process of the present invention, the maximum temperature of the catalyst layer is maintained to be at most 130° C. during the reaction with a view to suppressing formation of HFO-1243zf ($CF_3CH=CH_2$) as a by-product. That is, in the process of the present invention, an excessive temperature rise of the catalyst layer due to the heat of reaction generated by the reaction of the raw material mixed gas is suppressed, so that the maximum temperature of the catalyst layer will not exceed 130° C. The maximum temperature of the catalyst layer during the reaction is preferably at most 100° C., whereby it is easy to suppress formation of HFO-1243zf. Further, the maximum temperature of the catalyst layer during the reaction is preferably at least 60° C., more preferably at least 80° C., from the viewpoint of improvement of the conversion.

As a method for measuring the maximum temperature of the catalyst layer during the reaction, the following measuring method employing an insertion-type thermometer may, for example, be mentioned.

In the reaction of the raw material compound and the hydrogen in the catalyst layer, firstly, the catalyst at the raw material mixed gas inlet portion contributes to the reaction, and as the catalyst at the gas inlet portion deteriorates, the catalyst on the downstream side thereof will contribute to the reaction, and in such a manner, the reaction zone in the catalyst layer gradually moves towards to the gas outlet side. That is, the portion showing the maximum temperature of the catalyst layer during the reaction moves along with the movement of the reaction zone of the raw material mixed gas. Accordingly, by preliminarily positioning the measuring portion of the insertion-type thermometer at the gas inlet portion of the catalyst layer and moving the measuring portion along with the progress of the reaction, the maximum temperature of the catalyst layer during the reaction can be measured.

As a method to maintain the maximum temperature of the catalyst layer during the reaction to be at most 130° C., a method (method (α)) of introducing the hydrogen dividedly to the catalyst layer is preferred from such a viewpoint that the productivity can easily be maintained to be high while controlling the maximum temperature of the catalyst layer to be low. If the hydrogen is introduced dividedly to plural portions of the catalyst layer, it is possible to disperse the reaction zones of the raw material compound and the hydrogen in the catalyst layer without changing the amount of the raw material compound to be introduced, whereby generation of the heat of reaction is not localized at one portion. Therefore, it is possible to suppress local excessive heat generation in the catalyst layer and to easily maintain the maximum temperature of the catalyst layer to be at most 130° C., during the reaction without lowering the productivity.

The divided introduction of hydrogen means that at the same time as introducing the raw material compound and hydrogen to the gas inlet portion of the catalyst layer, hydrogen is introduced from at least one portion between the gas inlet portion and the gas outlet portion of the catalyst layer. That is, it means that hydrogen is introduced from at least one portion in the catalyst layer in addition to the inlet portion for introducing the raw material mixed gas, i.e. from a total of at least two positions.

Specifically, the raw material mixed gas to be introduced to the gas inlet portion (the gas inlet portion on the most upstream side in the gas flow direction) in the catalyst layer, is a mixed gas of the total amount of the raw material compound and a part of hydrogen to be introduced to the catalyst layer. The rest of hydrogen is introduced to the catalyst layer on the downstream side in the gas flow direction, and the hydrogen is mixed to a gas (usually a formed gas after a part of the raw material compound is reacted with hydrogen) flowing in the catalyst layer at the introduction position, and an unreacted raw material compound is reacted with hydrogen in the catalyst layer on the downstream side from the introduction position of the hydrogen, whereupon the formed gas is discharged from the outlet of the catalyst layer (the gas discharge portion on the most downstream side in the gas flow direction). It is preferred that at least a part of hydrogen in the raw material mixed gas is reacted with the raw material compound between the inlet portion of the raw material mixed gas and the next hydrogen introduction portion. Further, the hydrogen-introduction portion on the most downstream side in the gas flow direction is preferably provided at a position where the introduced hydrogen and the raw material compound can sufficiently be reacted in the catalyst layer between the hydrogen-introduction portion and the gas outlet portion.

Introduction of the hydrogen in the method (α) may be divided into two portions or divided into three or more portions. It is preferred to divide the introduction into two portions, whereby the process can be simplified. The divided proportions of the hydrogen to be introduced dividedly to at least two portions in the catalyst layer are preferably such that the respective gas amounts divided are equal amounts, whereby it is easy to maintain the maximum temperature of the catalyst layer to be low.

In a case where two or more portions packed with the catalyst-supporting carrier are present in the reactor, the divided introduction of hydrogen may, for example, be carried out by a method wherein a part of the hydrogen is introduced together with the raw material compound to the first stage packed portion, and the rest is introduced to the second and subsequent packed portions.

Further, as a method for controlling the maximum temperature of the catalyst layer other than the method (α), a method (method (β)) of letting an inert gas flow in the catalyst layer together with the raw material compound and the hydrogen, may be mentioned. By adjusting the concentration of the raw material compound and the hydrogen flowing in the catalyst layer by letting the inert gas flow, it is possible to suppress an excessive temperature rise of the catalyst layer by a heat of reaction. Further, a diluting gas other than the inert gas may be used instead of the inert gas or together with the inert gas.

As such an inert gas, nitrogen, rare gases or chlorofluorocarbons inert to the hydrogenation reaction may, for example, be mentioned. As the diluting gas other than the inert gas, hydrogen chloride may, for example, be mentioned.

The amount of the inert gas to be introduced to the catalyst layer is preferably at least 0.1 mol, more preferably at least 0.5 mol, per 1 mol of the raw material compound, from such a viewpoint that it is thereby easy to maintain the maximum temperature of the catalyst layer to be low, to reduce formation of by-products and to suppress deterioration of the catalyst. Further, the amount of the inert gas to be introduced is preferably at most 10 mol, more preferably at most 4 mol, per 1 mol of the raw material compound, from the viewpoint of the recovery rate of the inert gas.

Further, as a method for controlling the maximum temperature of the catalyst layer other than the method ($\alpha$) and the method ($\beta$), a method (method ($\gamma$)) may be mentioned wherein the temperature of the catalyst layer is made lower, while the lower limit is the dew point of the raw material mixed gas. By keeping the temperature of the catalyst layer to be low, a more swift heat removal of the heat of reaction becomes possible, and an excessive temperature rise of the catalyst layer can be suppressed. Further, the temperature of the catalyst layer during the reaction being lower, is advantageous in order to suppress formation of byproducts (such as HFO-1243zf) which are hardly separable from HFO-1234yf. In the method ($\gamma$), it is also preferred to adjust the temperature of the catalyst layer to be lower than 50° C. and higher than the dew point. In order to minimize formation of hardly separable byproducts, the temperature of the catalyst layer is preferably at most 40° C., more preferably at most 30° C.

As mentioned above, the temperature of the catalyst layer gradually decreases along with the progress of the deterioration of the catalyst, whereby the conversion may decrease. Therefore, also in the method ($\gamma$), it is preferred to carry out an operation to gradually raise the temperature of the heating medium so that the high conversion can be maintained and to keep the temperature of the catalyst layer at a sufficient level.

For the control of the maximum temperature of the catalyst layer, it is preferred to use the method ($\alpha$), the method ($\beta$) or the method ($\gamma$) alone, or two or three of them in combination. It is more preferred to use the method ($\alpha$) and the method ($\beta$) in combination.

The reaction pressure is preferably atmospheric pressure from the viewpoint of the operation efficiency.

The contact time of the raw material compound to the catalyst is preferably from 4 to 60 seconds, more preferably from 8 to 40 seconds. Such a contact time is a contact time of the raw material compound, which is calculated from the volume of the catalyst layer and the amount of the gas to be introduced to the reactor.

The ratio of the hydrogen to the raw material compound to be introduced to the catalyst layer is such that the ratio of the number of moles of the hydrogen to the number of moles of chlorine atoms in the raw material compound ($H_2$/Cl) is made to be preferably at most 0.7, more preferably at most 0.6, further preferably at most 0.5, from such a viewpoint that formation of by-products can thereby be easily suppressed. Further, the ratio ($H_2$/Cl) is preferably at least 0.1, more preferably at least 0.2, from the viewpoint of the yield of HFO-1234yf.

In a case where the hydrogen is dividedly introduced, with respect to the ratio of the total amount of hydrogen to be introduced to the catalyst layer to the raw material compound to be introduced to the catalyst layer, the above-mentioned ratio in the number of moles ($H_2$/Cl) is likewise adjusted to be preferably at most 0.7, more preferably at most 0.6, further preferably at most 0.5. Further, the ratio ($H_2$/Cl) is preferably at least 0.1, more preferably at least 0.2.

In the process of the present invention, the linear velocity u of the raw material compound represented by the following formula (I) in the catalyst layer, varies depending upon the diameter of the reaction tube, but in the case of the diameter of the reaction tube which is commonly used for a gas phase reduction reaction, it is preferably from 0.1 to 100 cm/sec., more preferably from 1 to 30 cm/sec. Such a linear velocity u is a linear velocity of the raw material compound which is calculated from the volume of the catalyst layer and the amount of the gas to be introduced to the reactor. When the linear velocity u of the raw material compound is at least the lower limit value, the productivity will be improved. Especially when the gas linear velocity is at least 1 cm/sec., the gas is likely to flow uniformly in the catalyst layer. When the linear velocity u of the raw material compound is at most the upper limit, the conversion of the raw material compound and the hydrogen will be improved. Especially when the gas linear velocity is at most 30 cm/sec., the temperature control in the vicinity of the reaction point due to heat generation will be easy.

$$u=(W/100) \times V/S \qquad (I)$$

In the formula (I), W is the concentration (mol %) of the raw material compound in the entire gas flowing through the catalyst layer, V is the flow rate ($cm^3$/sec) of the entire gas flowing through the catalyst layer, and S is the cross-sectional area ($cm^2$) of the catalyst layer to the flow direction of the gas.

As a reactor to be used for the process of the present invention, a known reactor capable of forming a catalyst layer having a catalyst packed, may be mentioned.

As the material for the reactor, glass, iron, nickel or an alloy containing such a metal as the main component may, for example, be mentioned.

The formed gas after the reaction contains, in addition to the desired product HFO-1234yf, an unreacted raw material, HCFO-1224yd formed as a reaction intermediate and HCl. Further, impurities contained in the formed gas are controlled to be within an allowable range for the process. The impurities contained in the formed gas may, for example, be HFO-1243zf, 1,1,1-trifluoropropane ($CF_3CH_2CH_3$, HFC-263fb), 1,1,1,2-tetrafluoropropane ($CF_3CHFCH_3$, HFC-254eb), 1-chloro-2,3,3,3-tetrafluoropropane ($CF_3CHFCH_2Cl$, HCFC-244eb) and 1,1-dichloro-2,3,3,3-tetrafluoropropane ($CF_3CHFCHCl_2$, HCFC-234ea).

In the present invention, HFO-1243zf in the formed gas excluding the diluting gas such as the inert gas, is preferably at most 10 volume ppm, and HCFC-234ea in the formed gas is preferably at most 10 volume ppm. According to the present invention, it is easy to suppress the amount of formation of these impurities, and particularly, it is possible to minimize the amount of HFO-1243zf contained in the formed gas.

HCl contained in the formed gas can be removed by blowing the formed gas into an alkali aqueous solution for its neutralization. The alkali to be used for such an alkali aqueous solution may, for example, be sodium hydroxide or potassium hydroxide.

As a method for recovering HFO-1234yf from the formed gas, a known method such as distillation may, for example, be employed.

The raw material compound is a gas composed of at least one of CFO-1214ya and HCFO-1224yd.

CFO-1214ya can be produced by a known method. For example, a method may be mentioned wherein 1,1-dichloro-2,2,3,3,3-pentafluoropropane ($CHCl_2CF_2CF_3$, HCFC-225ca) is subjected to a dehydrofluorination reaction by contacting it with an alkali aqueous solution in the presence of a phase-transfer catalyst. For such a reaction, a mixture of HCFC-225ca and its isomers may be used, and only HCFC-225ca in the mixture of isomers may selectively be dehydrofluorinated by the above phase-transfer catalyst. After the reaction, CFO-1214ya can be separated and recovered by a known method such as distillation. Further, one of compounds represented by $C_3HCl_2F_5$ or a mixture of two or more of them (i.e. a mixture of compounds which are isomers to one another) will be referred to as dichloropentafluoropropane (HCFC-225).

The above HCFC-225 can be produced by reacting tetrafluoroethylene and dichlorofluoromethane in the presence of a catalyst such as aluminium chloride. HCFC-225 obtainable by such a reaction contains HCFC-225ca and 1,3-dichloro-1,2,2,3,3-pentafluoropropane ($CHClFCF_2CClF_2$, HCFC-225cb) as the main components, and further contains a small amount of 2,2-dichloro-1,1,3,3,3-pentafluoropropane ($CHF_2CCl_2CF_3$, HCFC-225aa), 2,3-dichloro-1,1,2,3,3-pentafluoropropane ($CHF_2CClFCClF_2$, HCFC-225bb), etc.

As such HCFC-225, a commercial product may be employed. As such a commercial product, ASAHIKLIN AK225 (tradename, manufactured by Asahi Glass Company, Limited, mixture of 48 mol % of HCFC-225ca and 52 mol % of HCFC-225cb) may, for example, be mentioned.

As the above phase-transfer catalyst, tetrabutylammonium bromide (TBAB) is preferred.

Further, in the above production of CFO-1214ya, a recovered component after the separation and recovery by e.g. distillation usually contains, in addition to the raw material compound CFO-1214ya, a small amount of impurities being hydrochlorofluorocarbons such as $CF_3CF_2CH_2Cl$ (about 2.3 mol %), $CF_3CHFCH_2Cl$ (about 1.2 mol %), etc. In the process of the present invention, an impurity gas composed of such hydrochlorofluorocarbons may be present as mixed at the time of reacting the raw material compound with the hydrogen, so long as it is within a range not to impair the purpose of the present invention. That is, in the process of the present invention, the above-mentioned recovered component may be used as it is from the viewpoint of the productivity, etc.

The proportion of the impurity gas in the recovered component is preferably at most 10 mol %, more preferably at most 1 mol %, from such a viewpoint that highly pure HFO-1234yf can easily be thereby obtainable.

HCFO-1224yd is formed as an intermediate at the time of obtaining HFO-1234yf by reacting CFO-1214ya with hydrogen.

HCFO-1224yd recovered from the formed gas after the reaction may be reacted, as the raw material compound together with CFO-1214ya, with the hydrogen, or separately from CFO-1214ya, HCFO-1224yd may alone be reacted with the hydrogen.

In a case where a mixture of CFO-1214ya and HCFO-1224yd is used as the raw material compound, it is common to use a mixture having a small proportion of HCFO-1224yd, since HCFO-1224yd is an intermediate at the time of obtaining HFO-1234yf from the above CFO-1214ya. Accordingly, the proportion of HCFO-1224yd to the total amount of CFO-1214ya and HCFO-1224yd is preferably at most 50 mol %, more preferably at most 25 mol %.

According to the process of the present invention as described in the foregoing, in the reaction of the raw material compound and the hydrogen in the presence of the catalyst, the maximum temperature of the catalyst layer is maintained to be at most 130° C., whereby it is possible to suppress formation of HFO-1243zf which has a boiling point close to the desired product HFO-1234yf and thus is hardly separable by distillation. Therefore, it is possible to obtain highly pure HFO-1234yf.

EXAMPLES

Now, the present invention will be described in further detail with reference to Examples. However, it should be understood that the present invention is by no means restricted by the following description.

Example 1

Production of CFO-1214ya

CFO-1214ya ($CF_3CF\!=\!CCl_2$) was produced by the following method by using, as a reaction raw material, ASAHIKLIN AK225 (tradename, manufactured by Asahi Glass Company, Limited, mixture of isomers of HCFC-225 composed of HCFC-225ca ($CHCl_2CF_2CF_3$: 48 mol %) and HCFC-225cb ($CHClFCF_2CClF_2$: 52 mol %)) being dichloropentafluoropropane (HCFC-225).

Into a glass reactor having an internal capacity of 1 L and provided with a Dimroth condenser cooled to 0° C., 3 g of tetrabutylammonium bromide (TBAB) as a phase-transfer catalyst, 83 g (1.485 mol) of potassium hydroxide, 180 g of water, and 609 g (3.0 mol) of ASAHIKLIN AK225 were charged and then gradually heated with stirring, and a reaction was carried out at 45° C. for one hour. Thereafter, the reaction crude liquid phase-separated into two phases of an organic phase and an aqueous phase, was subjected to liquid separation. The organic phase was charged into a distillation column having an oven capacity of 1 L and an ability of theoretical number of plates of 10 plates, and distillation was carried out. As a result of the distillation, 262 g (1.43 mol) of CFO-1214ya (boiling point: 46° C.) having a purity of 99.5%, was obtained.

Example 2

For the production of HFO-1234yf ($CF_3CF\!=\!CH_2$), a reaction apparatus 101 shown in FIG. 1 was used.

As shown in FIG. 1, the reaction apparatus 101 is provided with two reaction tubes 110A and 110B and an oil bath 130 for immersion of such reaction tubes 110A and 110B. The reaction tube 110A has catalyst-packing portions 113a and 114a at two positions on the inlet 111a side and the outlet 112a side. Likewise, the reaction tube 110B has catalyst-packing portions 113b and 114b at two positions on the inlet 111b side and the outlet 112b side. The outlet 112a of the reaction tube 110A is connected by piping to the inlet 111b of the reaction tube 110B.

As the reaction tubes 110A and 110B, reaction tubes made of Inconel (registered trademark) 600 and having an inner diameter of 2.54 cm and a length of 100 cm, were used. Further, as a catalyst, a catalyst having 0.5 mass % of palladium supported on coconut shell active carbon, was used, and such a catalyst was packed in the catalyst-packing portion 114a on the outlet 112a side of the reaction tube 110A to form a catalyst layer 120A having a height of 40 cm. Likewise, the above catalyst was packed in the respective catalyst-packing portion 113b and 114b on the inlet 111b side and the outlet 112b side of the reaction tube 110B to form a catalyst layer 120B and a catalyst layer 120C each having a height of 40 cm. The packed density of the catalyst in catalyst layers 120A to 120C was adjusted to be 0.73 g/cm$^3$. In this Example, the catalyst-packing portion 113a was left to be vacant without packing the catalyst.

Then, the reaction tube 110A and the reaction tube 110B were immersed in the oil bath 130 so that all of the catalyst layers 120A to 120C were immersed, and the catalyst layers 120A to 120C were heated to 80° C.

A raw material compound (A) composed of CFO-1214ya ($CF_3CF\!=\!CCl_2$) obtained in Preparation Example 1, hydrogen (B) and nitrogen (C) were permitted to flow through reaction tubes 110A and 110B in a molar ratio of the total introduced amounts being hydrogen/CFO-1214ya/nitrogen=1/1/2 (ratio ($H_2$/Cl)=0.5). The contact time of the raw material compound (A) to the catalyst layers 120A to 120C was adjusted to be 17 seconds, and the linear velocity u of the raw material compound (A) was adjusted to be 7 cm/sec.

Further, with respect to the hydrogen (B), a part of the total introduced amount was introduced from the inlet 111a of the reaction tube 110A together with the raw material compound (A), and the rest was introduced to the piping portion connecting the reaction tube 110A and the reaction tube 110B. That is, in the catalyst layer (catalyst layer length 120 cm) consisting of catalyst layers 120A to 120C, the hydrogen (B) was dividedly introduced at two portions i.e. the catalyst layer 120A (0 cm point) and the catalyst layer 120B (40 cm point).

By adjusting the maximum temperature in the catalyst layers 120A to 120C by adjusting the divided proportions of the hydrogen (B) to be introduced to the catalyst layers, a relation between the maximum temperature of the catalyst layers 120A to 120C and the formed amount of HFO-1243zf as a by-product in the obtained formed gas (D), was examined. The maximum temperature of the catalyst layers 120A to 120C during the reaction was measured by insertion-type thermometers 140A to 140C inserted respectively to such catalyst layers.

Figure 2:
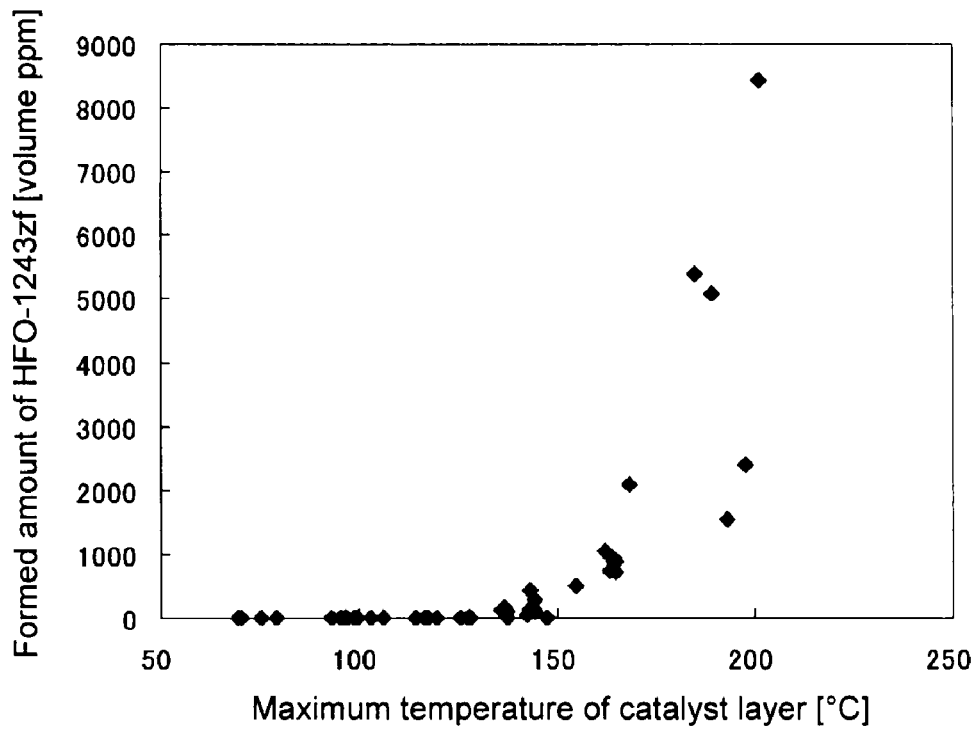
FIG. 2 is graphs showing the relation between the maximum temperature of the catalyst layer and the amount of the by-product formed in Examples.
Figure 2:
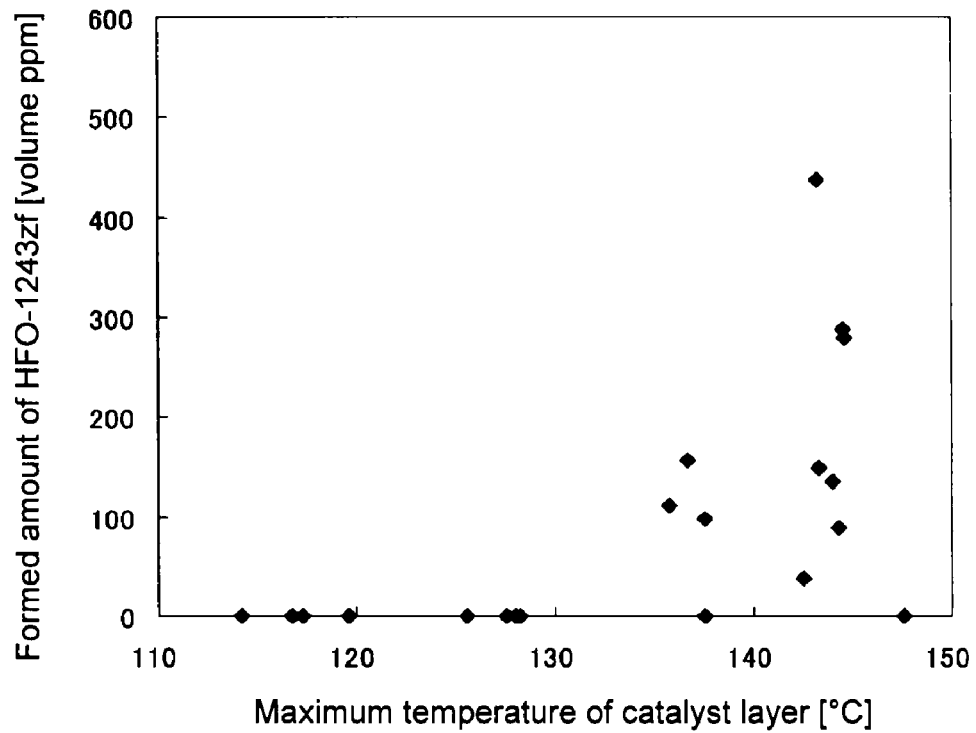

The relation between the maximum temperature of the catalyst layers 120A to 120C during the reaction and the formed amount of HFO-1243zf is shown in FIG. 2.

As shown in FIG. 2, HFO-1243zf was formed in a range where the maximum temperature in the catalyst layers 120A to 120C exceeded 130° C., while in the range where the maximum temperature was controlled to be at most 130° C., the content of HFO-1243zf in the formed gas (D) was at most 10 volume ppm (at most the detection limit by GC analysis).

Further, in a case where the maximum temperature in the catalyst layers 120A to 120C is 98° C., the contents of impurities other than HFO-1243zf in the formed gas (D) were, by GC area ratios, 0.1% of HFC-263fb, 3.0% of HFC-254eb, 0.1% of HCFC-244eb, and 0.04% of HCFC-234ea.

Further, the formed gas (D) when the maximum temperature in the catalyst layers 120A to 120C was 98° C., was analyzed by gas chromatography (GC), and the conversion ratio X (unit: %) from CFO-1214ya to HFO-1234yf was calculated by the following formula (II) and found to be 75%.

$$X=[Y/(Z/2)] \times 100 \quad \text{(II)}$$

(wherein Y is the number of moles of the formed HFO-1234yf, and Z is the number of moles of the introduced CFO-1214ya.)

Example 3

The same apparatus as in Preparation Example 2 was used. However, the reaction tube 110A and the reaction tube 110B were immersed in a salt bath/oil bath 130 so that all of the catalyst layers 120A to 120C were immersed, and the catalyst layers 120A to 120C were maintained at 30° C. A raw material compound (A) composed of CFO-1214ya ($CF_3CF=CCl_2$) obtained in Preparation Example 1, hydrogen (B) and nitrogen (C) were permitted to flow through the reaction tubes 110A and 110B in a molar ratio of the total introduced amounts being hydrogen/CFO-1214ya/nitrogen=1/1/7 (ratio ($H_2$/Cl)=0.5). The contact time of the raw material compound (A) to the catalyst layers 120A to 120C was adjusted to be 60 seconds, and the linear velocity u of the raw material compound (A) was adjusted to be 2 cm/sec.

After 6 hours from the initiation of the reaction, the maximum temperature of the catalyst layers was 121° C., and the content of HFO-1243zf in the formed gas (D) was at most 10 volume ppm (at most the detection limit by GC analysis).

Further, the contents of impurities other than HFO-1243zf in the formed gas (D) were, by GC area ratios, 1.4% of HFC-263fb and 5.0% of HFC-254eb.

Further, the formed gas (D) at that time was analyzed by gas chromatography (GC), and the conversion ratio X (unit: %) from CFO-1214ya to HFO-1234yf was calculated by the formula (II) and found to be 69%.

INDUSTRIAL APPLICABILITY

HFO-1234yf obtained by the process of the present invention has high purity, as formation of HFO-1243zf as a by-product is suppressed. Therefore, it is useful as e.g. a refrigerant to replace chlorofluorocarbons.

The entire disclosures of Japanese Patent Application No. 2010-142665 filed on Jun. 23, 2010 and U.S. Provisional Patent Application No. 61/365,966 filed on Jul. 20, 2010 including specifications, claims, drawings and summaries are incorporated herein by reference in their entireties.

REFERENCE SYMBOLS

101: Reaction apparatus
120A to 120C: Catalyst layers
A: Raw material compound
B: Hydrogen
C: Nitrogen
D: Formed gas

What is claimed is:

1. A process for producing 2,3,3,3-tetrafluoropropene, which comprises introducing and reacting a raw material compound composed of at least one of 1,1-dichloro-2,3,3,3-tetrafluoropropene and 1-chloro-2,3,3,3-tetrafluoropropene, and hydrogen, in a gas phase in a palladium catalyst layer packed with a catalyst-supporting carrier, wherein the temperature of the palladium catalyst layer is controlled to be higher than the dew point of the raw material mixed gas comprising the raw material compound and the hydrogen, and the maximum temperature of the palladium catalyst layer is maintained to be at most 130° C. during the reaction.

2. The process for producing 2,3,3,3-tetrafluoropropene according to claim 1, wherein the temperature of the palladium catalyst layer is at least 50° C.

3. The process for producing 2,3,3,3-tetrafluoropropene according to claim 1 or 2, wherein the catalyst-supporting carrier is active carbon.

4. The process for producing 2,3,3,3-tetrafluoropropene according to claim 3, wherein the amount of the palladium supported is from 0.1 to 10 mass % based on the active carbon.

5. The process for producing 2,3,3,3-tetrafluoropropene according to any one of claims 1 to 4, wherein the packed density of the catalyst-supporting carrier in the palladium catalyst layer is from 0.5 to 1 g/cm$^3$.

6. The process for producing 2,3,3,3-tetrafluoropropene according to any one of claims 1 to 4, wherein the palladium catalyst layer is maintained to be at most 80° C. except for the reaction zone of the raw material mixed gas and its vicinity in the palladium catalyst layer during the reaction.

7. The process for producing 2,3,3,3-tetrafluoropropene according to any one of claims 1 to 4, wherein the raw material mixed gas further contains an inert gas.

8. The process for producing 2,3,3,3-tetrafluoropropene according to any one of claims 1 to 4, wherein in the raw material mixed gas, the ratio of the number of moles of hydrogen to the number of moles of chlorine atoms in the raw material compound ($H_2$/Cl) is adjusted to be at most 0.7.

9. The process for producing 2,3,3,3-tetrafluoropropene according to any one of claims 1 to 4, wherein the hydrogen is introduced, as divided, to at least two positions in the palladium catalyst layer.

10. The process for producing 2,3,3,3-tetrafluoropropene according to claim 9, wherein the ratio of the total amount of hydrogen to the total amount of the raw material compound introduced to the palladium catalyst layer is adjusted to be at most 0.7 by the ratio of the number of moles of hydrogen to the number of moles of chlorine atoms in the raw material compound ($H_2$/Cl).

11. The process for producing 2,3,3,3-tetrafluoropropene according to any one of claims 1 to 4, wherein the linear velocity u of the raw material mixed gas represented by the following formula (I) in the catalyst layer is from 1 to 30 cm/sec.:

$$u = (W/100) \times V/S \tag{I}$$

(In the formula (I), W is the concentration (mol %) of the raw material compound in the entire gas flowing in the catalyst layer, V is the flow rate ($cm^3$/sec.) of the entire gas flowing in the palladium catalyst layer, and S is the cross-sectional area ($cm^2$) of the palladium catalyst layer to the flow direction of the gas.)

12. The process for producing 2,3,3,3-tetrafluoropropene according to claim 1, wherein the palladium catalyst is palladium, a palladium alloy, a mixture of palladium and another metal or a composite catalyst having palladium and another metal separately supported on carriers.

* * * * *